United States Patent [19]
Snyder

[11] Patent Number: 5,674,281
[45] Date of Patent: Oct. 7, 1997

[54] ARTIFICIAL HEART BRAKING SYSTEM

[75] Inventor: Alan J. Snyder, Hummelstown, Pa.

[73] Assignee: The Penn State Research Foundation, University Park, Pa.

[21] Appl. No.: 594,042

[22] Filed: Jan. 30, 1996

[51] Int. Cl.[6] .................................................. A61M 1/10
[52] U.S. Cl. ................................................ 623/3; 600/16
[58] Field of Search .............................. 600/16, 17, 18; 623/2, 3, 11, 66, 1, 900; 128/DIG. 3

[56] References Cited

PUBLICATIONS

Lau Siu–Wo, "An Experimental Study in Sensorless Commutation of the Penn State Artificial Heart", The Pennsylvania State University, Dec.1990.
Lau et al., "Sensorless Position Control of a Brushless Motor in Circulatory Assist Devices", Mechatronics vol. 1, No. 3, pp. 277–292, 1991.
Pae, Jr., et al., "Ventricular assist devices for postcardiotomy cardiogenic shock", The Journal of Thoracic and Cardiovascular Surgery, vol. 104, No. 3, Sep. 1992, pp. 541–553.
Pierce et al., "A long–term ventricular assist sytstem", The Journal of Thoracic and Cardiovascular Surgery, vol. 105, No. 3, pp. 520–524, Mar. 1993.
Poirier et al., "An Ambulatory, Intermediate Term Left Ventricular Assist Device", vol. XXXV Trans Am Soc Artif Intern Organs 1989, pp. 452–455.
Rintoul et al., "Continuing Development of the Cleveland Clinic–Nimbus total Artificial Heart", ASAIO Journal 1993, pp. M168–M171.
Rosenberg et al., "In Vivo Testing of a Clinical–size Totally Implantable Artificial Heart", Assisted Circulation 4, pp. 236–248, 1995.
Snyder, A Thesis in Bioengineering, "Automatic Electronic Control of an Electric Motor–Driven Total Artificial Heart", The Pennsylvania State University, The Graduate School, Bioengineering Program, Table of Contents and pp. 1–166, 1987.
Snyder et al., "Indirect Estimation of Circulatory Pressures For Control of an Electric Motor Driven Total Artificial Heart", pp. 87–88, 1985.
Snyder et al., "In Vivo Testing of a Completely Implanted Total Artificial Heart System", ASAIO Journal 1993; pp. M177–M184.
Tatsumi et al., "A Blood Pump with an interatrial Shunt for Use as an Electrohydraulic Total Artificial Heart", ASAIO Journal 1992, pp. M425–M430.
Weiss et al., "Progress Toward a Completely Implantable Left Ventricular Assist Device at the Pennsylvania State University", Assisted Circulation 4, pp. 124–137, 1995.
Yu et al., "A Compact and Noise Free Electrohydraulic Total Artificial Heart", ASAIO Journal 1993, pp. M386–M391.
The Institute of Electrical and Electronics Engineers Inc., Case Studies in Medical Instrument Design, "Development Of A Totally Implantable Artificial Heart Concept to Implementation", pp. 95–111, 1992.
The Institute of Electrical and Engineers Inc. Computer Society Press Reprint article, "Microcomputer Control of Permanently Implanted Blood Pumps", pp. 154–157, 1989.

*Primary Examiner*—John G. Weiss
*Assistant Examiner*—Francis K. Cuddihy
*Attorney, Agent, or Firm*—Marshall, O'Toole, Gerstein, Murray & Borun

[57] ABSTRACT

An artificial heart assembly, designed for implantation into a subject, which may be a total artificial heart or a ventricular assist device. The heart assembly has a blood inlet conduit, a blood outlet conduit, a pumping mechanism for pumping blood from the blood inlet conduit to the blood outlet conduit, and means for reversibly driving the pumping mechanism in a opposite directions over a stroke having a length defined by a pair of endpoints. The driving means has a motor which is braked by a braking means which has means for determining the actual speed of the pumping mechanism, means for comparing the actual speed of the pumping mechanism with a braking speed, and means for selectively applying the brake to the motor based upon the relative magnitudes of the actual speed and the braking speed.

28 Claims, 10 Drawing Sheets

ARTIFICIAL HEART BRAKING SYSTEM

This patent is subject to Government Contract No. N01-HV-88105 with the National Heart, Lung and Blood Institute and Grant No. R01-HL-13426 with the National Heart, Lung and Blood Institute.

BACKGROUND OF THE INVENTION

The present invention is directed to an artificial heart assembly having a motorized reciprocating pumping mechanism with a drive system that incorporates a brake to slow the pumping mechanism down as it approaches the ends of its stroke.

As defined herein, an artificial heart assembly intended for use with a subject, such as an animal or human, may be a total artificial heart (TAH) intended to replace the entire heart of the subject, a ventricular assist device (VAD) intended to replace a portion of the subject's heart, or an external blood pump to be used with the subject.

A conventional artificial heart has previously been provided with a DC motor to drive a pumping mechanism for pumping blood through the artificial heart. The DC motor has been provided with a stator and a permanent magnet rotor rotatable with respect to the stator, the rotor being connected to a coupler for translating the rotation of the rotor into linear movement of the blood pumping mechanism. The pumping mechanism reciprocates back and forth between two endpoints in a linear direction at a rate corresponding to that of a natural heartbeat.

It has previously been proposed to incorporate a "brake" into the system for driving the DC motor so that the pumping mechanism is slowed as it approaches both ends of its stroke. The operation of the brake was described by Dr. Alan Snyder in a graduate thesis entitled "Automatic Electronic Control of an Electric Motor-Driven Total Artificial Heart" dated May 1987 as follows: "At a preplanned distance, $n_b$, before the diastolic endpoint, $n_d$, a dynamic brake is applied to the motor (all leads shorted by the power switch). If, through any band between the brake point and the diastolic endpoint, the measured velocity is less than half the desired velocity, $n_b$ is decremented, so that the brake is applied later on the ensuing cycle. If the device overshoots the diastolic endpoint, $n_b$ is decremented, so that the brake is applied sooner on the next cycle." However, the above manner of applying the brake was found to be unacceptable since it resulted in premature failure of the artificial heart.

SUMMARY OF THE INVENTION

The invention is directed to an artificial heart assembly having a blood inlet conduit, a blood outlet conduit, a pumping mechanism for pumping blood from the blood inlet conduit to the blood outlet conduit, and means for reversibly driving the pumping mechanism in a opposite directions over a stroke having a length defined by a pair of endpoints. The driving means has a motor which is selectively braked. The means for braking the motor includes means for determining the actual speed of the pumping mechanism, means for comparing the actual speed of the pumping mechanism with a braking speed, and means for selectively applying the brake to the motor based upon the relative magnitudes of the actual speed and the braking speed.

The artificial heart assembly may be provided with a stall detector in the form of a plurality of position sensors which periodically generate a position code based on the angular position of the rotor of the motor with respect to the stator and means for determining whether the position sensors have generated a position code within a predefined period of time. Upon the detection of a stall, the braking means removes the brake if it was previously applied. Consequently, the braking means may repeatedly apply and remove the brake during a single stroke of the pumping mechanism.

The pumping mechanism may be translatable through a plurality of position bands between its endpoints; the means for determining the actual speed of the pumping mechanism may determine the actual speed in one of the position bands of the pumping mechanism; the braking means may store a plurality of braking speeds, each of which is associated with a different position band; and the comparing means may compare the actual speed of the pumping mechanism in the one position band with the braking speed associated with the one position band.

One of the stored braking speeds associated with one of the position bands may be increased upon the detection of a motor stall to reduce the likelihood of a motor stall in the next stroke in the same direction. One of the stored braking speeds may be decreased upon the detection that the pumping mechanism moved past one of the endpoints to reduce the likelihood that the pumping mechanism will move past that endpoint in a subsequent stroke.

The invention is also directed to a method of operating an artificial heart assembly having a blood inlet conduit, a blood outlet conduit, and a pumping mechanism for pumping blood from the blood inlet conduit to the blood outlet conduit. The method includes the steps of: reversibly driving the pumping mechanism in opposite directions over a stroke having a length defined by a pair of endpoints, determining the actual speed of the pumping mechanism, comparing the actual speed of the pumping mechanism with a braking speed, and selectively applying a brake to the pumping mechanism based upon the relative magnitudes of the actual speed and the braking speed.

The method may also include the steps of detecting a motor stall and removing the brake upon the detection of a motor stall. The pumping mechanism may be driven through a plurality of position bands between the endpoints; the artificial heart assembly may have a plurality of braking speeds stored therein, each braking speed being associated with a different position band; and the actual speed of the pumping mechanism in the one position band may be compared with the braking speed associated with that position band to determine whether the brake should be applied.

The method may also include the steps of detecting a motor stall and increasing one of the braking speeds associated with one of the position bands upon detection of the stall, and detecting when the pumping mechanism moves past one of the endpoints and decreasing one of the braking speeds associated with one of the position bands upon detection that the pumping mechanism moved past the endpoint.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
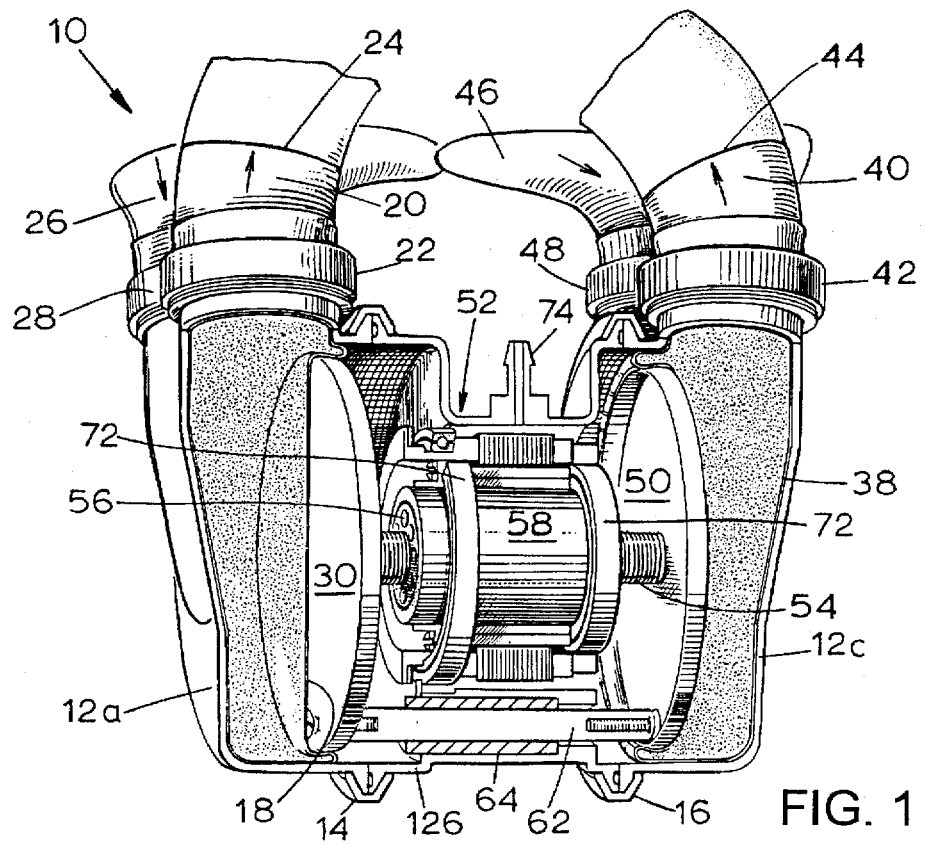
FIG. 1 is a perspective view of an artificial heart, portions of which are shown in cross section.

FIG. 1 illustrates an artificial heart assembly 10 intended to be completely implanted within a subject, such as a human or an animal, to take the place of the subject's natural heart. The artificial heart 10 has a housing 12 composed of three sections 12a, 12b, 12c which are held together by a pair of annular V-rings 14, 16.

A blood reservoir within a sac 18 disposed within the housing section 12a is fluidly coupled to a blood outlet defined by an artificial vascular graft 20 connected to the housing section 12a via a threaded connector 22. The graft 20 is connected to the pulmonary artery of the subject via a suture line 24. The blood reservoir 18 is fluidly coupled to a blood inlet chamber defined by an artificial graft 26 which is connected to the housing section 12a via a threaded connector 28 and to the right atrium of the subject via a suture line (not shown). A pair of one-way check valves (not shown) are disposed in the blood inlet 26 and the blood outlet 20 to ensure that blood is pumped in the direction shown by the arrows in FIG. 1. A pusher plate 30 makes contact with and periodically deforms the blood sac 18 to force blood from the blood inlet 26 to the blood outlet 20.

A blood sac 38 disposed within the housing section 12c is fluidly coupled to a blood outlet defined by an artificial graft 40 connected to the housing section 12c via a threaded connector 42. The graft 40 is connected to the aorta of the subject via a suture line 44. The blood reservoir 38 is coupled to a blood inlet chamber defined by an artificial graft 46 which is connected to the housing section 12c via a threaded connector 48 and to the left atrium of the subject via a suture line (not shown). A pair of one-way check valves (not shown) are disposed in the blood inlet 46 and the blood outlet 40 to ensure that blood is pumped in the direction shown by the arrows. A pusher plate 50 makes contact with and periodically deforms the blood sac 38 to force blood from the blood inlet 46 to the blood outlet 40.

The pusher plates 30, 50, which form part of a pump mechanism, are driven laterally back and forth by a DC brushless motor 52 coupled to the pusher plates 30, 50 via a drive screw 54 and a coupling mechanism composed of a plurality of threaded elongate rollers 56 disposed within a cylindrical nut 58 fixed to a rotor (not shown) of the motor 52. Rotation of the rotor causes the nut 58 and rollers 56 to rotate, thus causing the drive screw 54 to be linearly displaced in a direction parallel to its longitudinal central axis. A guide rod 62 is connected between the two pusher plates 30, 50 and passes through a fixed bushing 64 to prevent the plates 30, 50 from rotating. Other mechanisms for coupling the rotor to the pusher plates 30, 50 could be used.

The rotation of the rotor is controlled via the electrical energization of a plurality of windings of a stator (not shown) which is rotatably coupled to the rotor via a pair of cylindrical bearings 72. A wire port 74 is formed in the housing section 12b to allow the passage of wires from the windings to a microcontroller 100 (FIG. 2), which may be implanted in another area of the subject, such as in the subject's abdomen.

ARTIFICIAL HEART ELECTRONICS

Figure 2A:
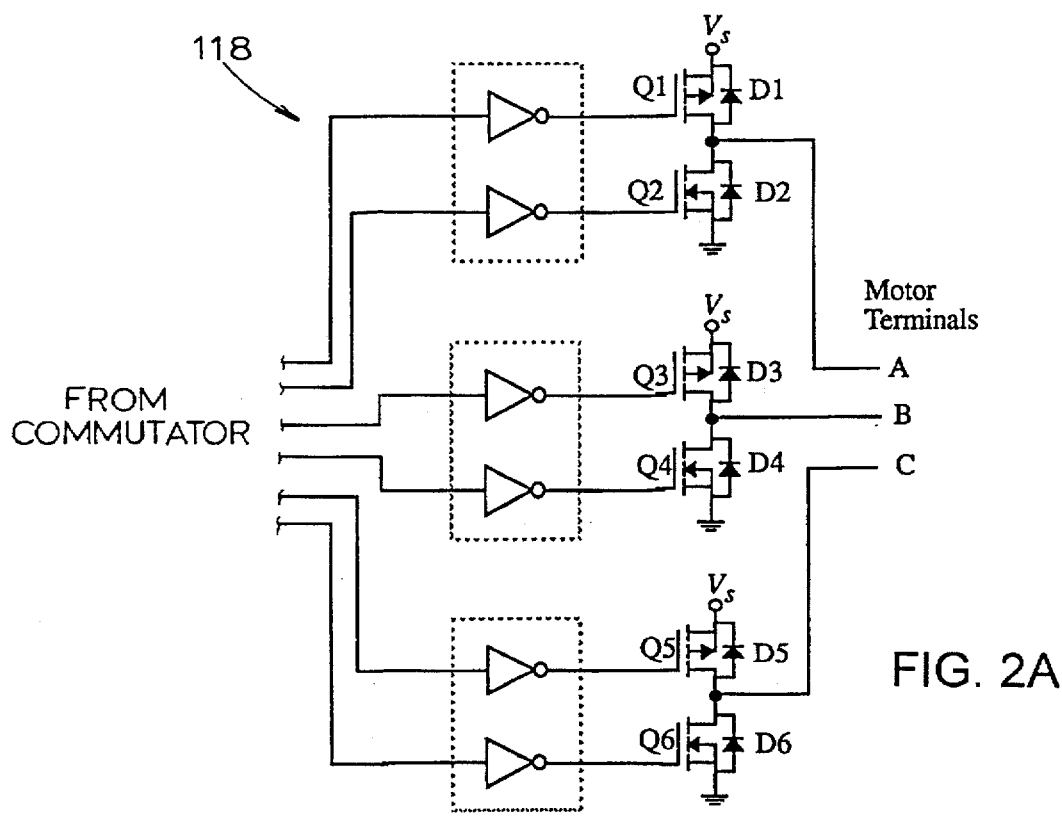
FIG. 2A is a circuit diagram of the driver circuit shown schematically in FIG. 2.
Figure 2:
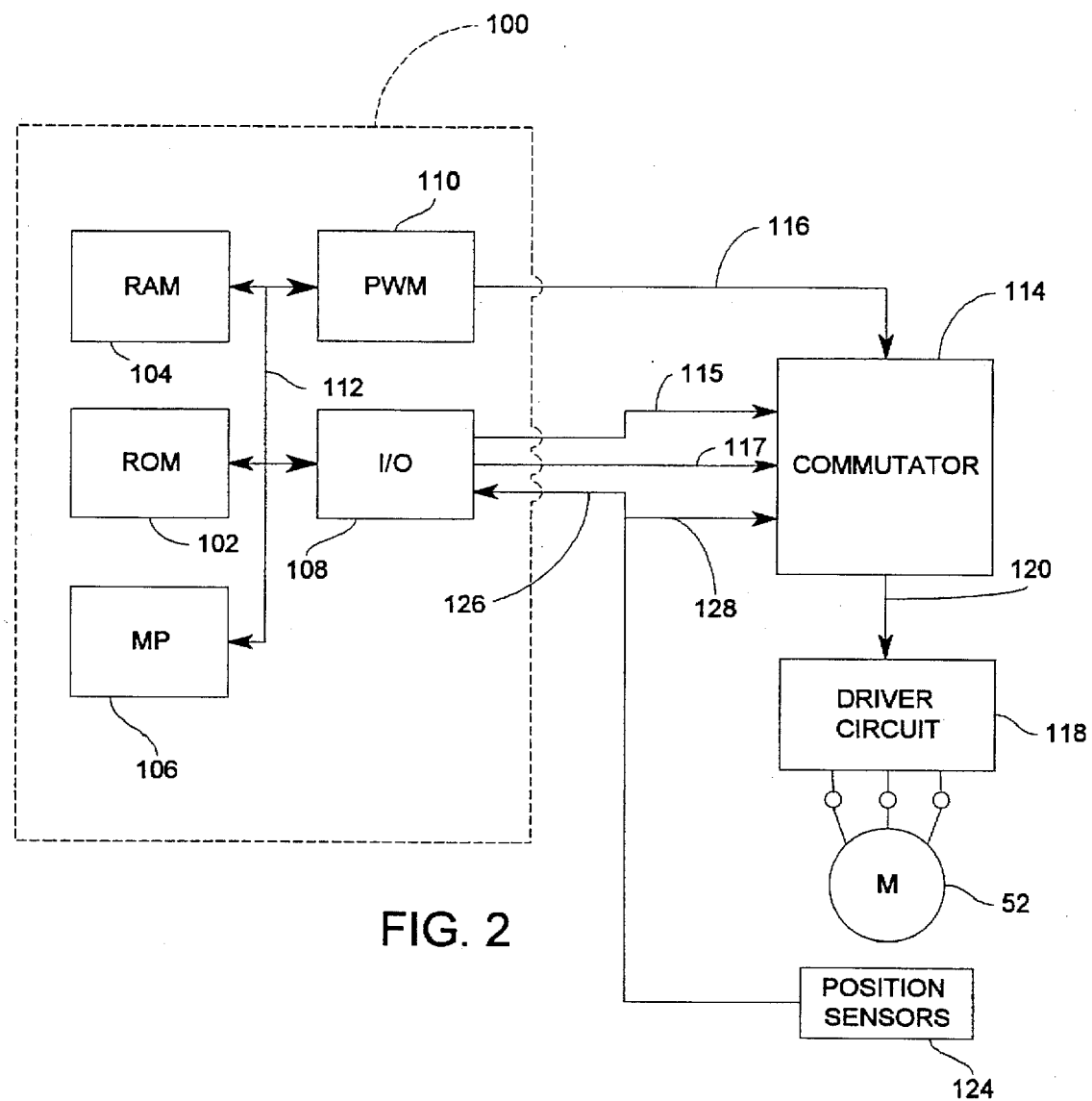
FIG. 2 is a block diagram of the electronics portion of the artificial heart of FIG. 1.

Referring to FIG. 2, the controller 100, which may be a conventional integrated circuit chip, has a read-only memory (ROM) 102, a random-access memory (RAM) 104, a microprocessor (MP) 106, a conventional input/output (I/O) circuit 108, and a conventional pulse-width modulator (PWM) circuit 110, all of which are interconnected via an address and data bus 112.

The controller 100 is operatively connected to a commutator circuit 114 which periodically generates a set of commutation signals which are transmitted to a driver circuit 118 via a line 120. The driver circuit 118 generates a set of electrical drive signals that are transmitted to the stator windings of the motor 52 via three lines connected to three terminals of the motor 52.

The commutator 114 is provided with a PWM signal from the PWM circuit 110 via a line 116, a direction signal from the I/O circuit 108 via a line 115 which specifies which direction the motor 52 should be driven, and a brake signal from the I/O circuit 108 via a line 117 which indicates when the "brake" should be applied.

As shown in FIG. 2A, the driver circuit 118 may be composed of three pairs of switching transistors Q1–Q6, each pair having a first transistor with one terminal connected to a voltage source and a second terminal connected to one of the motor terminals and a second transistor with one terminal connected to the same motor terminal and a second terminal connected to ground. Each transistor has a third control terminal which is provided with a control signal from a MOSFET driver (shown in the dotted boxes) that controls whether the current path across its first and second terminals is conductive or nonconductive.

When the brake signal is sent to the commutator 114 via the line 115, the driver circuit 118 brakes the motor 52. This braking may be accomplished, for example, by causing the transistors Q2, Q4, Q6 to become simultaneously conductive so that all three motor terminals are connected to ground via a conductive path through those transistors. This braking of the motor 52 causes it to slow at a relatively fast rate, which slows the motor 52 more quickly than just not providing drive signals to the motor 52.

Three position sensors 124, such as Hall-effect sensors, are associated with the motor 52 and generate a set of position signals that are indicative of the angular position of the rotor with respect to the stator. The position signals are transmitted to the I/O circuit 108 via a line 126 and to the commutator 114 via a line 128.

OVERALL OPERATION

During operation of the artificial heart 10, the commutator 114 periodically generates a set of commutation signals and transmits them to the driver circuit 118 to drive the motor 52. The commutation signals are generated in a conventional manner based upon a three-bit position signal generated by the position sensors 124 and based upon a PWM signal generated by the PWM circuit 110. The duty cycle or pulse width of the PWM signal controls the amount of acceleration of the motor 52, with a relatively large duty cycle corresponding to a relatively high rate of acceleration and a relatively small duty cycle corresponding to a relatively low rate of acceleration.

Figure 3:
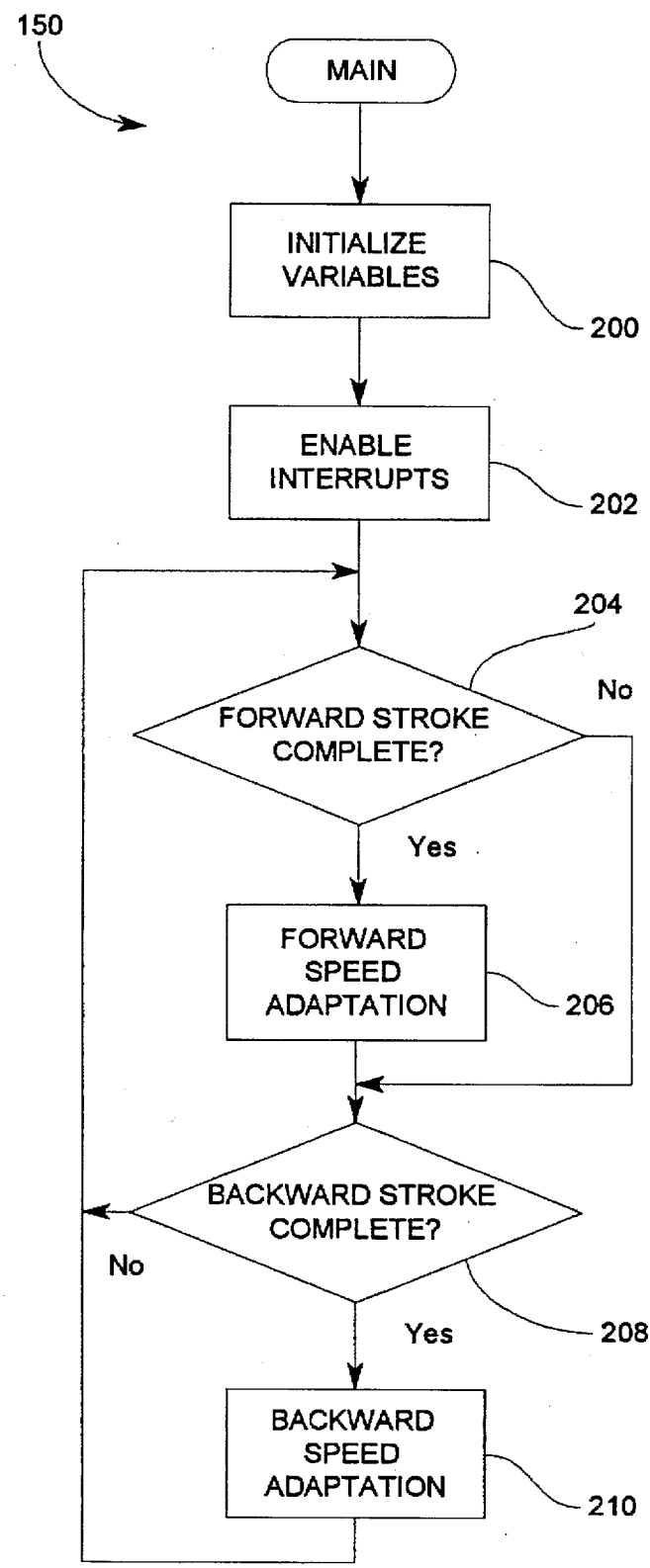
FIG. 3 is a flowchart of the overall operation of the drive control system of the artificial heart.

FIG. 3 is a flowchart of a computer program, stored in the ROM 102 (FIG. 2) and executed by the microprocessor 106, that: 1) determines the duty cycle of the PWM signal to control the acceleration of the motor 52, and 2) determines when the motor 52 should be braked. The performance of these two functions facilitates the motor's ability to reciprocate the pump mechanism (i.e. the drive screw 54 and the attached pusher plates 30, 50) back and forth at a relatively high rate, in excess of 30 times per minute, to pump blood through the artificial heart 10 along the flow pathways described above. In the absence of the braking function, the speed at which the motor 52 was driven would have to be reduced.

Referring to FIG. 3, at step 200 a number of variables are initialized, and at step 202 the interrupts which may be generated during operation are enabled. These interrupts include a sensor interrupt which is generated each time the position sensors 124 generate a position signal and a stall interrupt which is generated when the rotational speed of the rotor falls below a lower speed threshold, as described below.

Steps 204–210 are continuously repeated during operation so that, after the completion of each full stroke of the pump mechanism, either a forward or a backward speed adaptation is performed, depending on whether the forward stroke (e.g. from left to right in FIG. 1) or the backward stroke was completed.

Steps 204, 208 detect the completion of the forward and backward strokes by a software position counter which counts the number of rotational increments of the motor 52 (as described below, the position sensors 124 generate a position code for each successive increment), with the two ends of linear motion coinciding with fixed increment counts, e.g. the left end of the stroke coinciding with a count of zero and the right end of the stroke coinciding with a count of 198 (33 bands×6 increments per band).

SPEED ADAPTATION ROUTINES

The purpose of the speed adaptation routines 206, 210 is to vary the pulse width of the PWM signal provided to the commutator 114 by the PWM circuit 110 so that the pump mechanism is driven at an actual speed which corresponds to a desired speed.

Each time the rotor of the motor 52 moves through a predetermined increment of rotation, a three-bit position code is generated by the position sensors 124 and a sensor interrupt is generated. A position "band" is defined herein as a predetermined number of rotational increments, e.g. six increments of rotation, in which case the motor 52 would move through a complete band after six sensor interrupts are generated. A complete stroke of the pump, in either the forward or backward direction, is composed of a number of position bands, such as 33 position bands.

For each band in the forward stroke, a desired speed is specified via a desired speed table, a portion of one example of which is set forth below. The values in the following table are exemplary only, and the real values used should be based on the specific motor and pump mechanism used.

| DESIRED SPEED TABLE | |
|---|---|
| BAND | DESIRED SPEED |
| 23 | 90 |
| 24 | 90 |
| 25 | 90 |
| 26 | 90 |
| 27 | 70 |
| 28 | 50 |
| 29 | 35 |
| 30 | 25 |
| 31 | 20 |
| 32 | 15 |
| 33 | 5 |

Thus, in band 28, the desired speed (e.g. linear travel of the pump mechanism in millimeters per second) is specified to be 50.

A backward speed table having the same configuration is used to specify the desired speed for each band in the backward direction since the desired speeds may not be symmetrical in both directions due to the unequal forces encountered by the pump mechanism in the two directions.

The software also includes a pair of actual speed tables, one for each direction, which store the actual speed of the pump at each band during the previous stroke, and a pair of pulse width tables, one for each direction, that store the pulse width of the PWM signal to be generated by the PWM circuit 110 during each band. The desired speed tables may be stored in the ROM 102, and the actual speed and pulse width tables are stored in the RAM 104.

Figure 4:
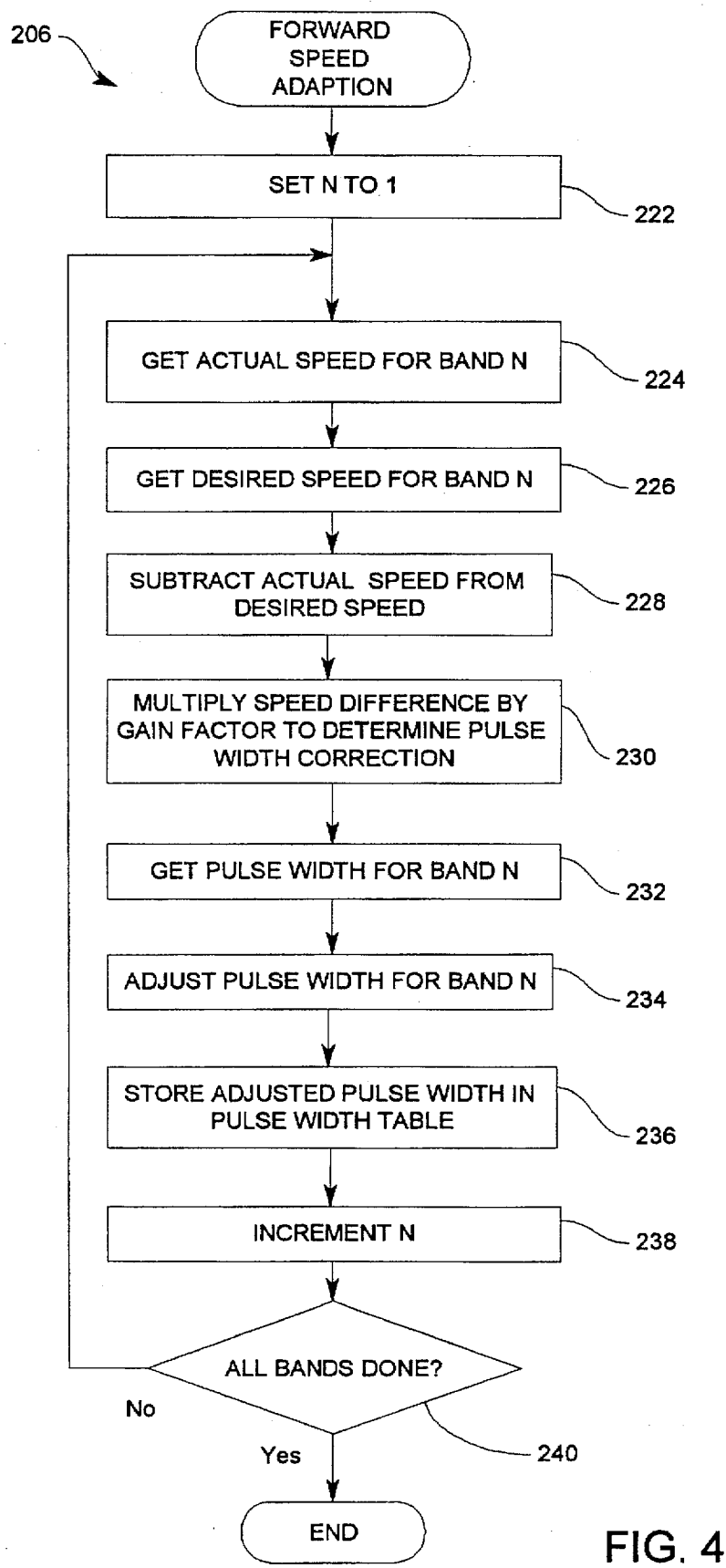
FIG. 4 is a flowchart of a forward speed adaptation routine shown schematically in FIG. 3.

FIG. 4 is a flowchart of the forward speed adaptation routine 206 shown schematically in FIG. 3. Referring to FIG. 4, the forward speed adaptation routine 206 begins at step 222, where a variable N is set to 1 to specify the first band in the forward stroke direction. At step 224, the actual speed of the pump for the band specified by N is retrieved from the actual speed table for the forward direction. At step 226, the desired speed of the pump for the band specified by N is retrieved from the desired speed table for the forward direction.

At step 228, the actual speed for the specified band is subtracted from the desired speed for the specified band, and at step 230 that speed difference is multiplied by a gain factor (i.e. a constant) to calculate a pulse-width correction. At step 232, the pulse width (i.e. duty cycle) currently specified for the band N is retrieved from the pulse width table, and at step 234 that pulse width is adjusted by adding to it the pulse-width correction determined at step 230. At step 236, the adjusted pulse width determined is stored in the band N position in the pulse width table for the current direction, replacing the previous value of the pulse width for that band.

At step 238, the variable N is incremented, and at step 240, if the pulse widths for all the bands have not been adjusted, the program branches back to step 224 where the process is repeated for the next band specified by the new value of N.

The operation of the backward speed adaptation step 210 is identical to that of the forward speed adaptation routine 206 described above, except that instead of increasing the variable N from 1 to its maximum value, N is decreased from its maximum value to 1. Also, the backward speed adaptation step 210 accesses the desired and actual speed tables and the pulse width table for the backward direction.

SENSOR ROUTINE

Figure 5:
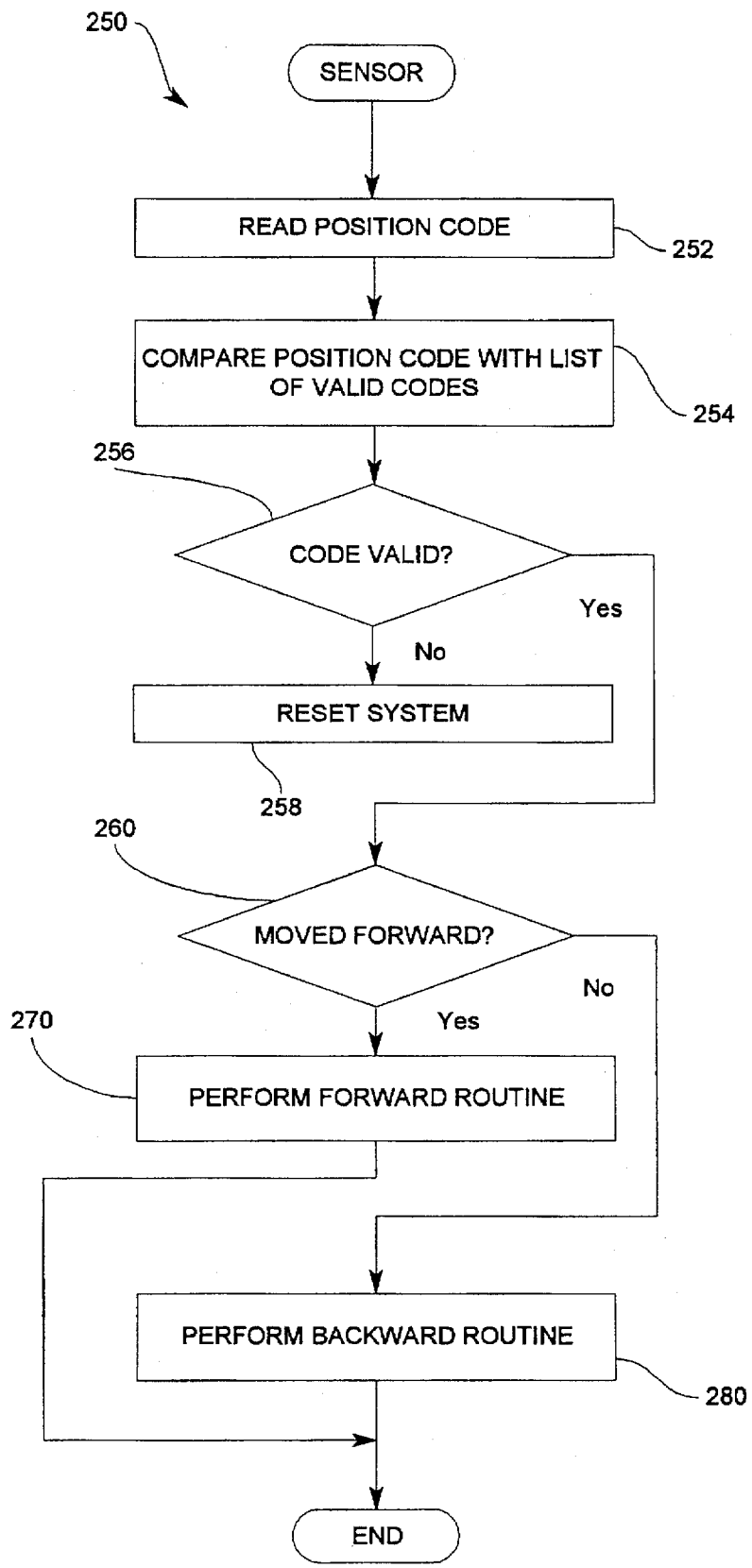
FIG. 5 is a flowchart of a sensor routine periodically performed during operation of the artificial heart.

FIG. 5 is a flowchart of a sensor interrupt service routine 250 that is performed each time of sensor interrupt is generated. When invoked, the sensor routine 250 temporarily interrupts the performance of the main routine 150.

Referring to FIG. 5, at step 252, the position code generated by the sensors 124 is read. For successive angular increments of the rotor, the sensors 124 generate a unique 3-bit position code, such as those set forth in the table below:

| POSITION CODE TABLE | |
|---|---|
| INCREMENT | POSITION CODE |
| 1 | 000 |
| 2 | 001 |
| 3 | 011 |
| 4 | 111 |
| 5 | 110 |
| 6 | 100 |

At step 254, the position code read at step 252 is compared with a list of six valid position codes (there are two position codes that do not correspond to a position). At step 258, if the position code read at step 252 does not match one of the six valid codes, the program branches to step 258 where the controller 100 is reset, after which the operation begins again at step 200 of the main routine 150.

If the position code was valid, the program branches to step 260, where it is determined whether the pump moved in the forward or backward direction. This is determined by comparing the current position code (read during the current execution of step 252) with the two position codes in the position code table before and after the position code that was read during the prior execution of step 252. For example, referring to position code table set forth above, if the position code read during the previous execution of step 252 was 111 (Increment 4), then the pump moved forward if the current position code read is 110 (Increment 5), or the pump moved backward if the current position code is 011 (Increment 3).

If the pump moved forward as determined at step 260, the program branches to step 270 where a forward routine (shown in FIG. 6) is performed. Otherwise, the program branches to step 280 where a backward routine (FIG. 7) is performed.

FORWARD AND BACKWARD ROUTINES

Figure 6:
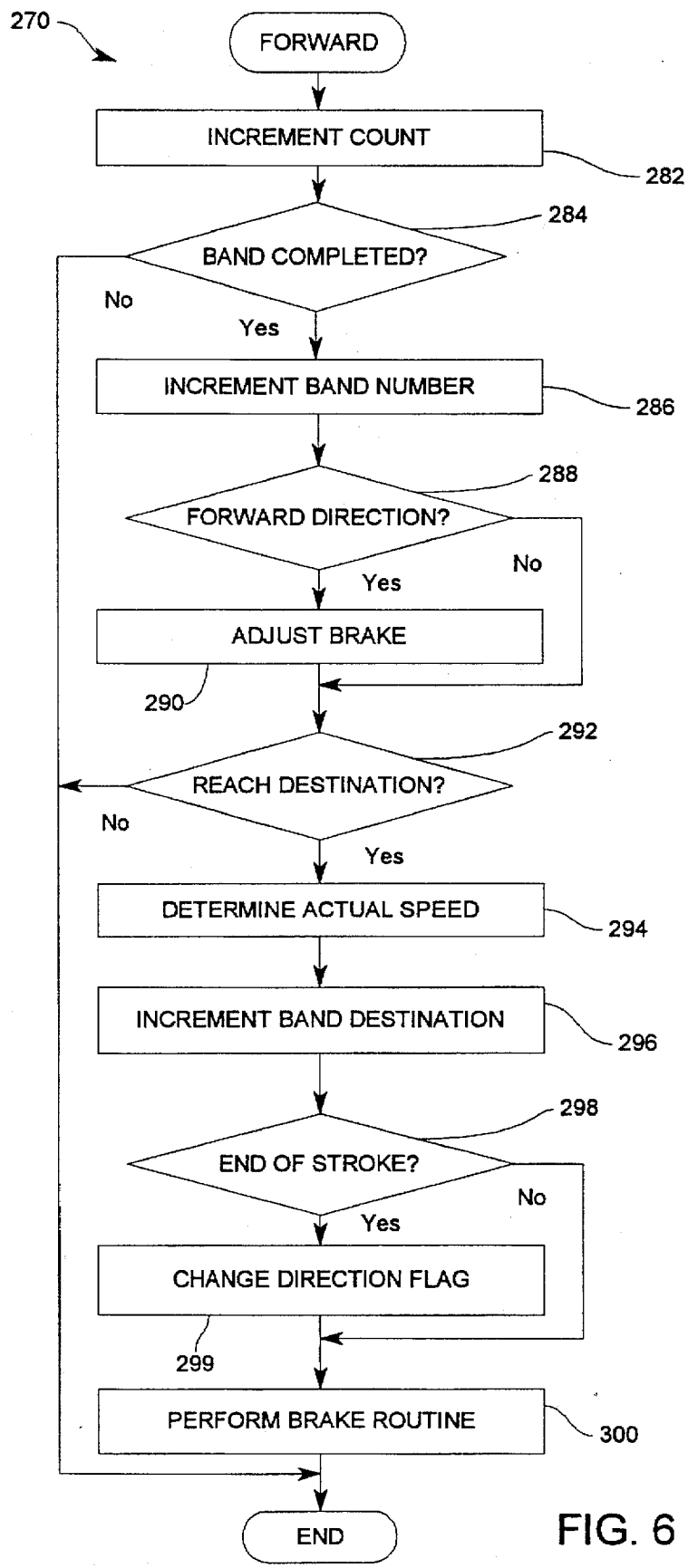
FIG. 6 is a flowchart of a forward routine shown schematically in FIG. 5.

A flowchart of the forward routine 270 is shown in FIG. 6. The forward routine 270 performs a number of basic tasks, including keeping track of the current position of the pump and measuring the actual speed of the pump.

At step 282, a modulo-six software counter (since one position band is defined as six angular increments) is incremented by one since the position sensors 124 have just detected angular movement of the rotor. As is known, a modulo-six counter automatically resets itself to zero upon reaching a count of six. Step 284 determines whether a band is completed by checking to determine whether the count of the modulo-six counter is zero. If a band has not been completed, the program skips steps 286-300, which are performed only upon the completion of a band.

If a band has just been completed, the program branches to step 286 where the band number (which represents the current band position) is incremented. At step 288, the program determines whether the pump is supposed to be moving in the forward direction by checking the value of a direction flag. In unusual cases, it is possible for the pump to be moving in the wrong direction, for example, due to a fluid pressure surge opposite the movement direction which cannot be overcome by the motor 52. If the pump is supposed to be moving in the forward direction, the program branches to step 290 where a brake adjust routine, described below, is performed.

At step 292, the program determines whether the pump reached its intended destination. This is determined by comparing the current band number (set at step 286) with the expected band destination (which was previously set at step 296). For example, if the pump is moving in the forward direction and the current band number is 25, then the expected band destination is 26. When the next band is completed, the current band number will be incremented by one to 26 at step 286, and will equal the expected band destination of 26 (which will subsequently be incremented to 27 at step 296 to represent the next expected band destination). In unusual circumstances, it is possible that the pump did not reach its expected destination due to a pressure surge in the opposing direction.

If the pump did reach its expected destination as determined at step 292, then the program branches to step 294 where the actual speed of the pump is determined. The actual speed is determined based on measuring the time that elapses between the completion of successive bands (by reading a system clock (not shown) contained in the controller 100). After the actual speed for the band just completed is determined, the actual speed is stored in the actual speed table described above. At step 296, the band destination is incremented.

Step 298 determines whether the end of the stroke has been reached by determining whether the upper band number, e.g. 33, has been reached. If so, the program branches to step 299 where the direction flag is changed to indicate that the pump should be driven in the reverse direction, and at step 302, a brake routine described below is performed.

Figure 7:
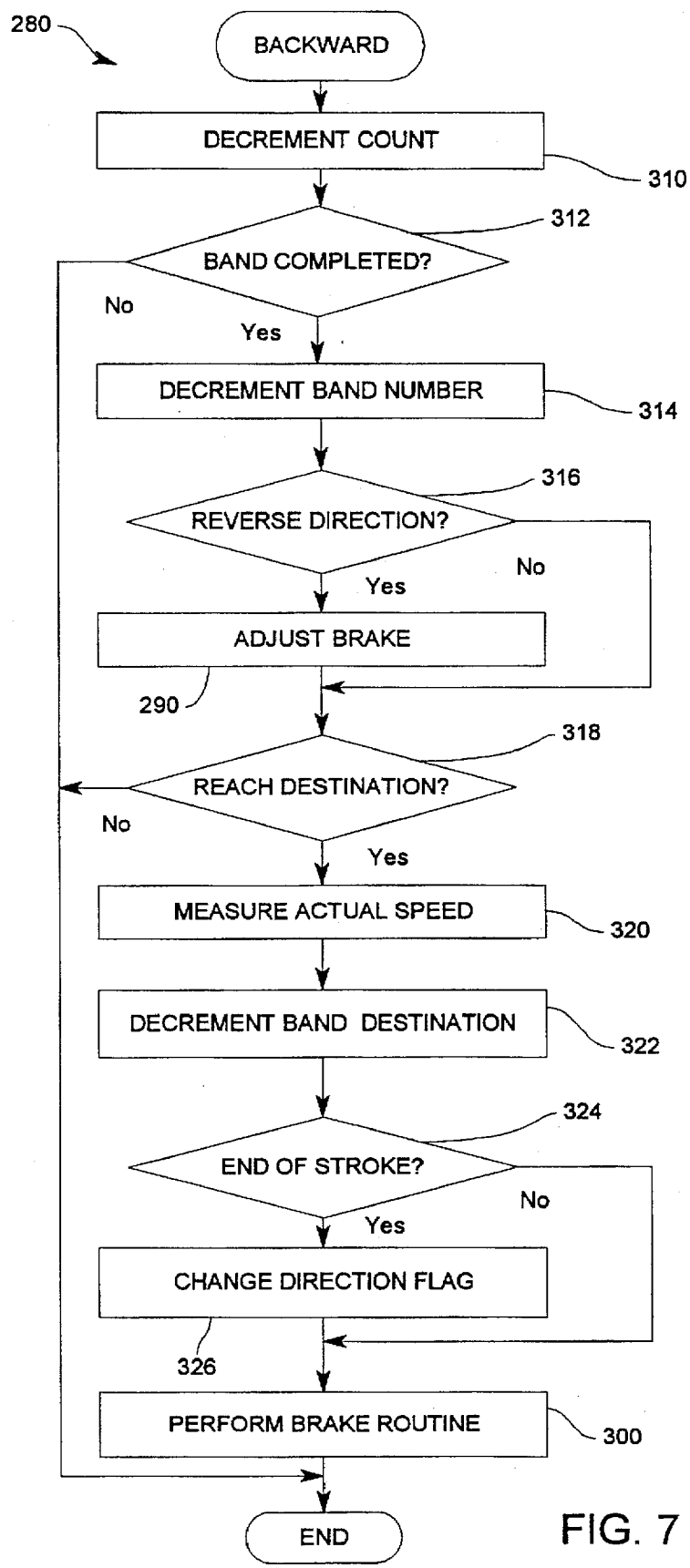
FIG. 7 is a flowchart of a backward routine shown schematically in FIG. 5.

The operation of the backward routine 280 shown in FIG. 7 is substantially the same as the forward routine 270 just described, except that the modulo-six counter counts down at step 310 of FIG. 7 and the band number and destination are decremented at steps 314, 322 of FIG. 7.

ADJUST BRAKE ROUTINE

Figure 8:
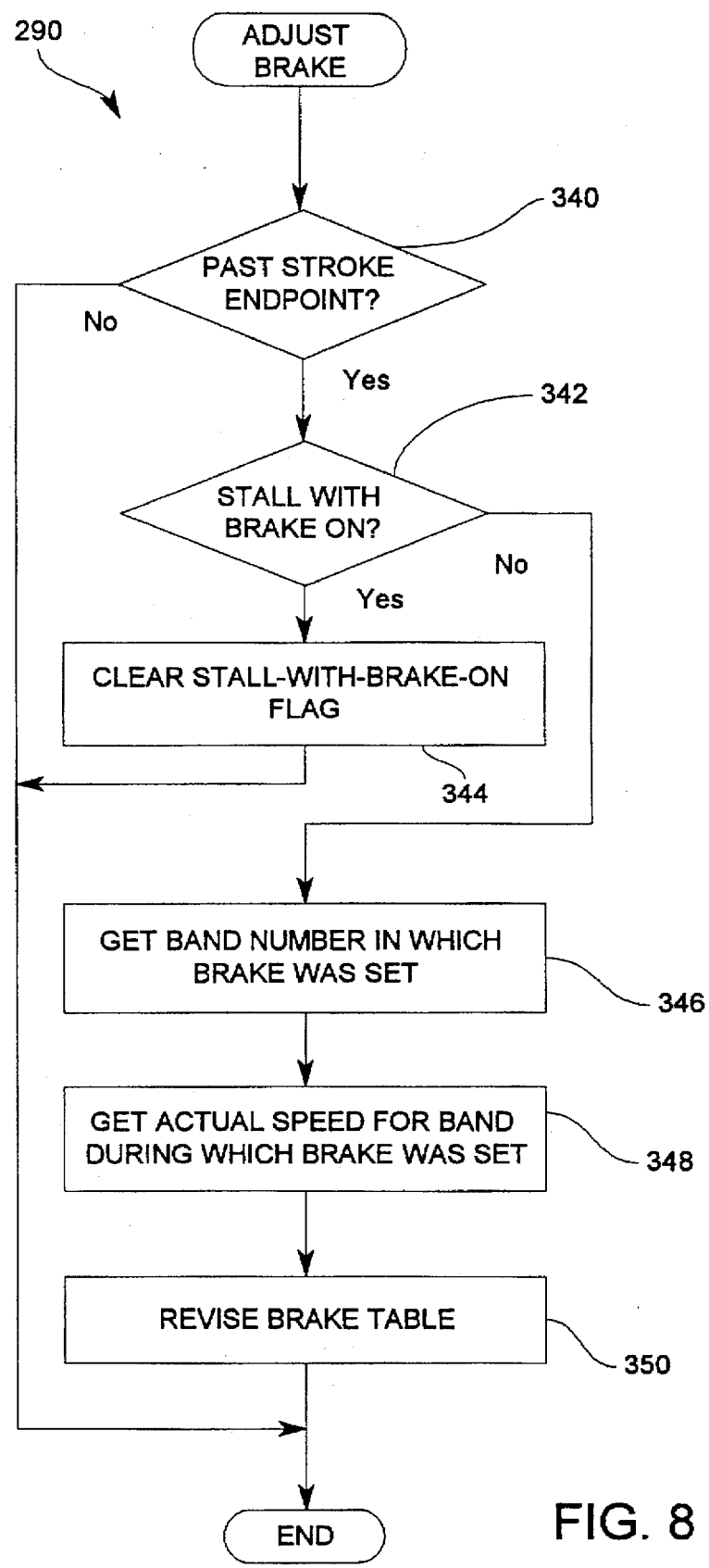
FIG. 8 is a flowchart of an adjust brake routine shown schematically in FIG. 7.

FIG. 8 is a flowchart of the adjust brake routine shown schematically as step 290 in FIGS. 6 and 7. The basic function performed by the adjust brake routine 290 is to alter the position during the stroke at which the brake is applied.

Referring to FIG. 8, step 340 determines if the pump is past its stroke endpoint by comparing the current band number with the upper band limit (e.g. 33) for the forward direction or comparing the current band number with the lower band limit (e.g. 1) for the backward direction.

At step 342, if the motor 52 stalled with the brake on, which is determined by checking the status of a stalled-with-brake-on flag, the program branches to step 344 where the stalled-with-brake-on flag is cleared. If the motor 52 did not stall with the brake on as determined at step 342, the program branches to step 346.

Steps 346-350 act to cause the brake to be applied one band earlier (assuming the pump approaches the endpoint at the same speed during the next stroke), so that the pump is less likely to move past its stroke endpoint during the next stroke in the same direction. At step 346, the program retrieves from memory the number of the position band in which the brake was first applied. At step 348, the program retrieves from the actual speed table the actual speed for the band during which the brake was first set.

Then, at step 350, a brake table (there is a separate brake table for each direction) which determines when the brake is applied during a stroke, is revised to cause the brake to be put on one band earlier in the next stroke in the same direction since the pump moved past its stroke endpoint (as determined at step 340). Referring to the table set forth below, for each of a number of bands adjacent the end of a stroke, the brake table stores a braking speed. If the actual speed of the pump during any band surpasses the braking speed for that band, the brake is applied. For example, if the actual speed for the band 30 was 32, the brake would be applied since the actual speed was in excess of the braking speed.

| BRAKE TABLE | |
|---|---|
| BAND | BRAKING SPEED |
| 23 | 100 |
| 24 | 100 |
| 25 | 100 |
| 26 | 100 |
| 27 | 100 |
| 28 | 50 |
| 29 | 40 |
| 30 | 30 |
| 31 | 24 |
| 32 | 21 |
| 33 | 11 |

At step 350, the braking speed for the band just prior to the band in which the brake was applied is increased to the actual speed for that band minus one. Thus, if the brake was applied in band 30 and the actual speed in band 29 was 37, the braking speed for band 29 would be changed from 40 to 36, in which case (assuming the actual speed for the next stroke in the same direction was the same), the brake would be put on in band 29 instead of in band 30, and the pump would be less likely to move past its endpoint.

BRAKE ROUTINE

Figure 9:
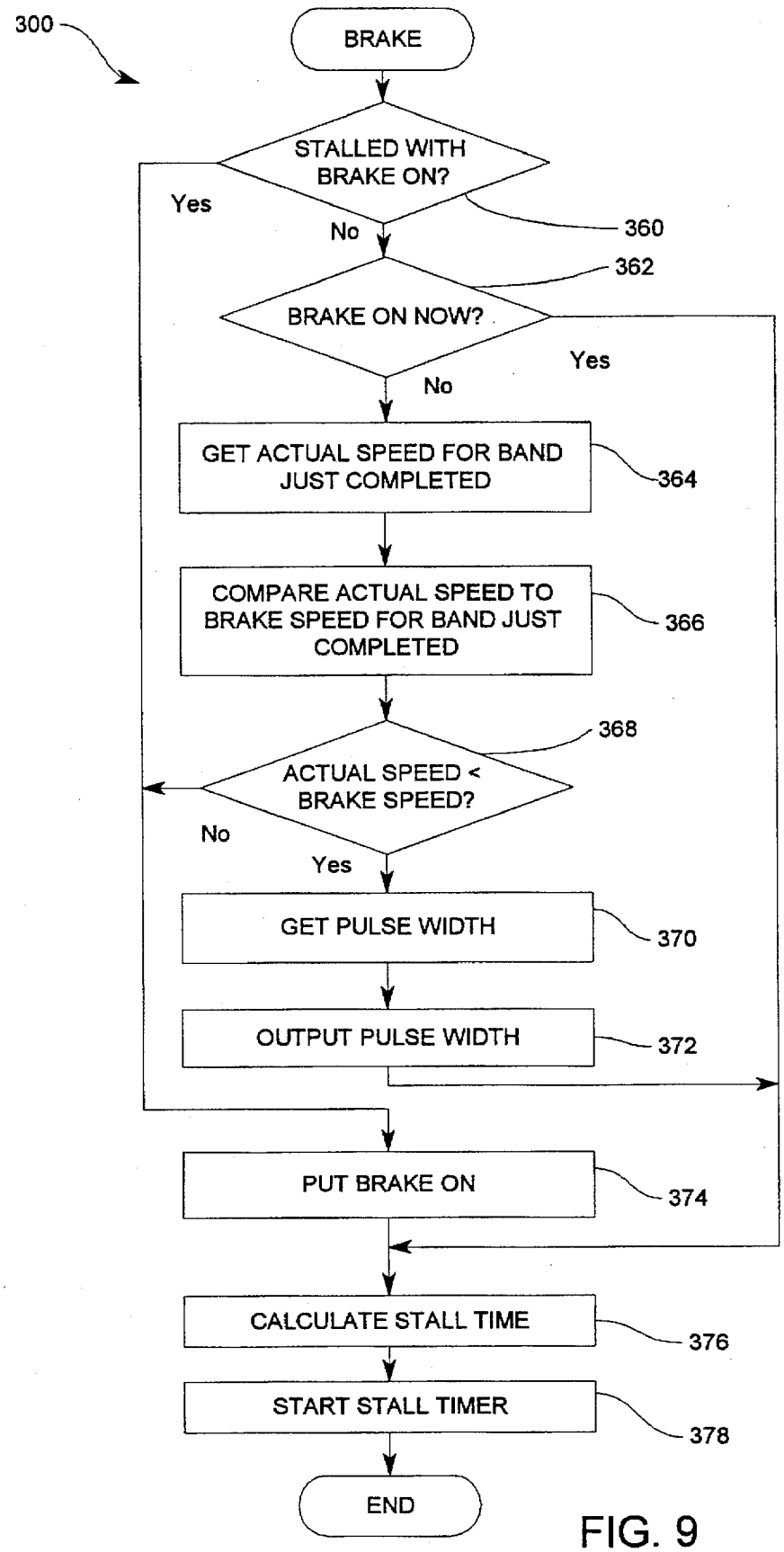
FIG. 9 is a flowchart of a brake routine shown schematically in FIG. 7.

FIG. 9 is a flowchart of the operation of the brake routine 300 shown schematically in FIG. 7. The basic function of the brake routine 300 is to apply the brake if the pump is moving too fast for a particular band and to reapply, or "pump," the brake if a previous application of the brake caused the motor to stall.

Referring to FIG. 9, step 360 determines (by checking the stalled-with-brake-on flag) if the motor stalled with the brake on. That would occur if a previous execution of the brake routine 300 caused the brake to be applied during a stroke and if the application of the brake caused the motor to stall. In the case of a stall, the brake is removed (as described below in connection with FIG. 10), so that if the motor stalled with the brake on as determined at step 360, the brake would not be on. In that case, the program branches to step 374 where the brake is reapplied.

If the motor did not stall with the brake on, the program branches to step 362. At step 362, if the brake is not on, the program branches to steps 364–368 where it determines whether the brake should be applied because the pump is moving too fast for the current band. In particular, at step 364 the actual speed for the band just completed is retrieved from the actual speed table, and at step 366 that actual speed is compared with the braking speed for the band just completed (from the brake table for the current direction). At step 368, if the actual speed is not less than the braking speed, the program branches to step 374 where the brake is applied.

If the actual speed is less than the braking speed, the program branches to steps 370–372 where the desired pulse width of the PWM signal sent to the commutator 114 is transmitted to the PWM circuit 110. This is accomplished by retrieving at step 370 the pulse width for the next band from the pulse width table for the current direction (as described above in FIG. 6, the brake routine 300 is only performed upon completion of a band as determined at step 284) and transmitting that pulse width to the PWM circuit 110 at step 372.

STALL ROUTINE

Figure 10:
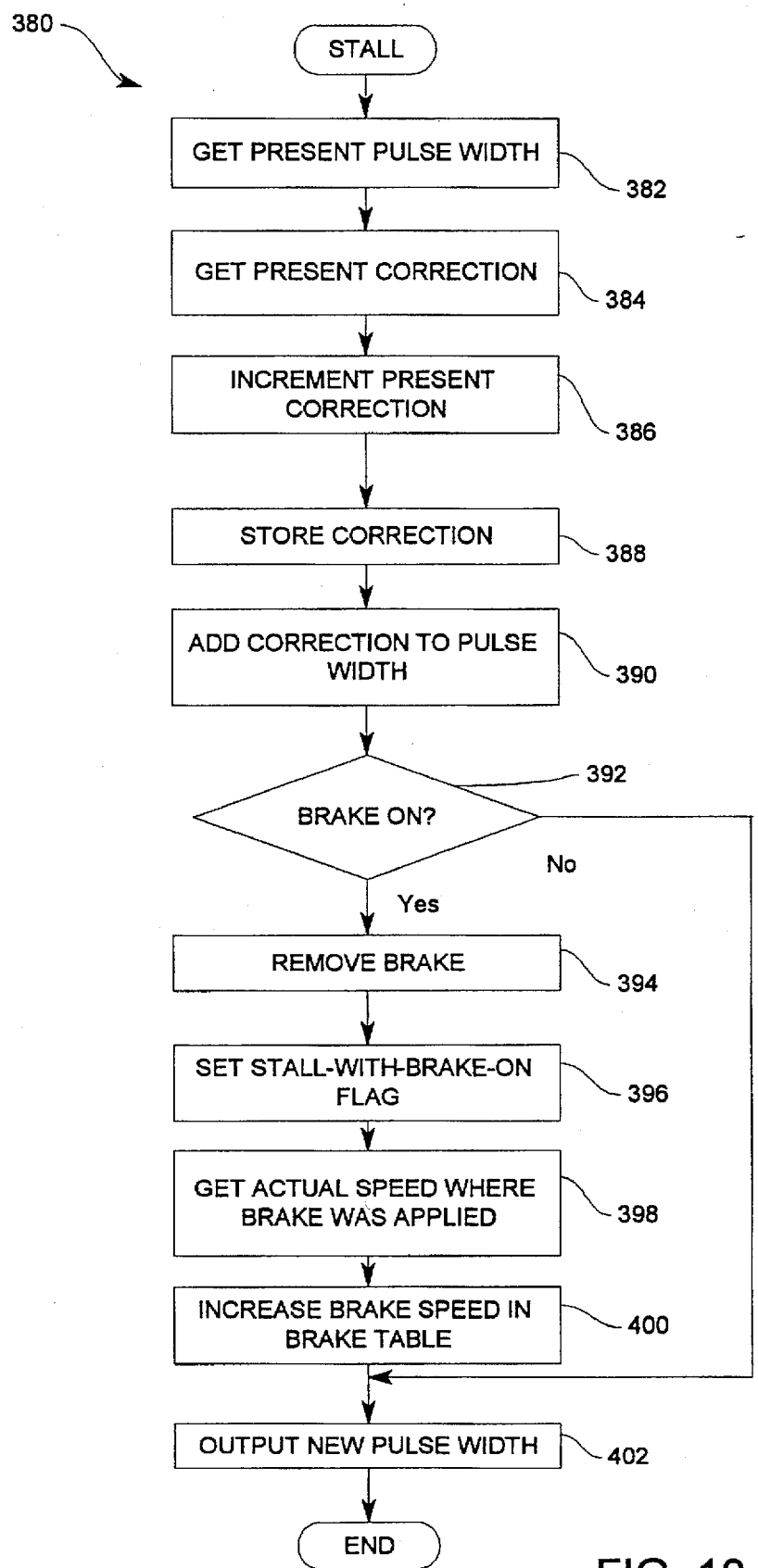
FIG. 10 is a flowchart of a stall routine that may be performed during operation of the artificial heart.

A flowchart of a stall interrupt service routine 380 is shown in FIG. 10. The stall routine 380 is performed upon the occurrence of a stall interrupt, which is automatically generated when the position sensors 124 fail to generate a new position code after a predetermined time period elapses. The predetermined time period, which is measured by a stall timer, is selected to be twice the estimated completion time for the next band. The estimated completion time for the next band is determined based upon the desired speed of the pump in that band.

The stall routine 380 performs a number of functions, including modifying the pulse width of the PWM signal in an attempt to prevent a future stall and to modify the brake table to attempt to prevent a future stall due to the application of the brake.

Referring to FIG. 10, at step 382 the present pulse width for the current band is retrieved from the pulse width table for the current direction. At step 384, the present pulse width correction is retrieved. If the stall routine is being performed for the first time, this correction is zero. If the stall routine has already been performed at least once for this band, the present correction is the value stored at step 388 during the most recent execution of the stall routine 380.

At step 386, the present correction retrieved at step 384 is incremented by a predetermined amount (e.g. by an amount which causes the duty cycle of the PWM signal to increase by 7%), and the new correction is stored at step 388. At step 390, the new correction is added to the pulse width stored in the pulse width table for the current band and direction.

At step 392, if the brake is on, meaning that the application of the brake caused the stall, the program branches to step 394 where the brake is removed and then to step 396 wherein the stall-with-brake-on flag is set. Steps 398–400 are then performed to cause the brake to be applied later in the next stroke to prevent a stall (assuming the actual speed of the pump as it approaches the endpoint is the same during the next stroke). At step 398, the actual speed in the band in which the brake was applied is retrieved from the actual speed table for the current direction, and at step 400 the braking speed in the brake table for that band and direction is increased. In particular, the braking speed for that band is made equal to one more than the actual speed for that band so that (assuming the actual speed is the same during the next stroke in the same direction) the brake will not be applied in the same band of the next stroke. At step 402, the new pulse width determined at step 390 is transmitted to the PWM circuit 110.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. An artificial heart assembly, comprising:
    a blood inlet conduit;
    a blood outlet conduit;
    a pumping mechanism for pumping blood from said blood inlet conduit to said blood outlet conduit;
    means for reversibly driving said pumping mechanism in a first direction and a second direction over a stroke having a length defined by a pair of stroke endpoints, said pumping mechanism being moveable through a plurality of position bands between said endpoints, said pumping mechanism being capable of changing between said first and second directions at a rate of at least 30 times per minute and having an actual speed which varies over said stroke, said driving means including a motor; and
    means coupled to said driving means for braking said motor, said braking means comprising:
        means for determining said actual speed of said pumping mechanism in one of said position bands of said pumping mechanism;
        means for storing a plurality of braking speeds, each of said braking speeds being associated with a different one of said position bands including said one position band;
        means for comparing said actual speed of said pumping mechanism in said one position band with said braking speed associated with said one position band; and
        means for selectively applying a brake to said motor based upon the relative magnitudes of said actual speed and said braking speed.

2. The artificial heart assembly as defined in claim 1 additionally comprising:
    means for detecting a motor stall; and
    means for increasing one of said braking speeds stored in said storing means upon the detection of a motor stall.

3. The artificial heart assembly as defined in claim 1 additionally comprising:
    means for detecting when said pumping mechanism moves past one of said endpoints; and
    means for decreasing one of said braking speeds stored in said storing means upon the detection of said pumping mechanism moving past one of said endpoints.

4. The artificial heart assembly as defined in claim 1 wherein said braking means comprises means for repeatedly applying and removing said brake during a single stroke of said pumping mechanism based upon said actual speed of said pumping mechanism.

5. The artificial heart assembly as defined in claim 1 additionally comprising means for detecting a motor stall and wherein said braking means comprises means for removing said brake upon the detection of a motor stall by said stall-detecting means.

6. The artificial heart assembly as defined in claim 1 additionally comprising a membrane defining a blood chamber fluidly coupled to said blood inlet conduit and said blood outlet conduit, wherein said pumping mechanism comprises a pusher plate which makes contact with said membrane to force blood from said blood inlet conduit to said blood outlet conduit.

7. The artificial heart assembly as defined in claim 1 additionally comprising:
    a first membrane defining a blood chamber fluidly coupled to said blood inlet conduit and said blood outlet conduit, wherein said pumping mechanism comprises a pusher plate which makes contact with said first membrane to force blood from said blood inlet conduit to said blood outlet conduit;
    a second membrane defining a second blood chamber fluidly coupled to a second blood inlet conduit and a second blood outlet conduit; and
    a second pusher plate which makes contact with said second membrane to force blood from said second blood inlet conduit to said second blood outlet conduit.

8. An artificial heart assembly, comprising:
    a blood inlet conduit;
    a blood outlet conduit;
    a pumping mechanism for pumping blood from said blood inlet conduit to said blood outlet conduit;
    means for reversibly driving said pumping mechanism in a first direction and a second direction over a stroke having a length defined by a pair of stroke endpoints, said pumping mechanism having an actual speed which varies over said stroke, said driving means including a motor; and
    means coupled to said driving means for braking said motor, said braking means comprising:
        means for determining said actual speed of said pumping mechanism;
        means for comparing said actual speed of said pumping mechanism with a braking speed; and
        means for selectively applying a brake to said motor based upon the relative magnitudes of said actual speed and said braking speed.

9. The artificial heart assembly as defined in claim 8 wherein said motor comprises a plurality of motor terminals and wherein said braking means comprises means for connecting all of said motor terminals to ground.

10. The artificial heart assembly defined in claim 8 additionally comprising means for detecting a motor stall.

11. The artificial heart assembly as defined in claim 10 wherein said driving means comprises a DC brushless motor having a stator and a rotor with an angular position that varies with respect to said stator and wherein said stall-detecting means comprises:
    means for periodically generating a position code based on said angular position of said rotor with respect to said stator; and
    means for determining whether said code-generating means has generated a position code within a predefined period of time.

12. The artificial heart assembly as defined in claim 8 additionally comprising means for detecting a motor stall and wherein said braking means comprises means for removing said brake upon the detection of a motor stall by said stall-detecting means.

13. The artificial heart assembly as defined in claim 8 wherein said braking means comprises means for repeatedly applying and removing said brake during a single stroke of said pumping mechanism based upon said actual speed of said pumping mechanism.

14. The artificial heart assembly as defined in claim 8,
    wherein said pumping mechanism is moveable through a plurality of position bands between said endpoints;
    wherein said means for determining said actual speed of said pumping mechanism comprises means for determining said actual speed of said pumping mechanism in one of said position bands of said pumping mechanism;

wherein said braking means additionally comprises means for storing a plurality of braking speeds, each of said braking speeds being associated with a different one of said position bands including said one position band; and wherein said comparing means comprises means for comparing said actual speed of said pumping mechanism in said one position band with said braking speed associated with said one position band.

15. The artificial heart assembly as defined in claim 14 additionally comprising means for modifying one of said braking speeds stored in said storing means.

16. The artificial heart assembly as defined in claim 14 additionally comprising:

means for detecting a motor stall; and means for increasing one of said braking speeds stored in said storing means upon the detection of a motor stall.

17. The artificial heart assembly as defined in claim 14 additionally comprising:

means for detecting when said pumping mechanism moves past one of said endpoints; and means for decreasing one of said braking speeds stored in said storing means upon the detection of said pumping mechanism moving past one of said endpoints.

18. The artificial heart assembly as defined in claim 8 wherein said means for selectively applying said brake comprises means for selectively applying said brake when said actual speed is greater than said braking speed.

19. The artificial heart assembly as defined in claim 8 wherein said driving means comprises a DC brushless motor with a stator and a rotor having a rotational speed and wherein said means for determining said actual speed of said pumping mechanism comprises means for determining said actual speed of said pumping mechanism based upon said rotational speed of said rotor.

20. The artificial heart assembly as defined in claim 19 wherein said means for determining said actual speed of said pumping mechanism comprises a plurality of position sensors.

21. The artificial heart assembly as defined in claim 8 additionally comprising a membrane defining a blood chamber fluidly coupled to said blood inlet conduit and said blood outlet conduit, wherein said pumping mechanism comprises a pusher plate which makes contact with said membrane to force blood from said blood inlet conduit to said blood outlet conduit.

22. The artificial heart assembly as defined in claim 8 additionally comprising:

a first membrane defining a blood chamber fluidly coupled to said blood inlet conduit and said blood outlet conduit, wherein said pumping mechanism comprises a pusher plate which makes contact with said first membrane to force blood from said blood inlet conduit to said blood outlet conduit;

a second membrane defining a second blood chamber fluidly coupled to a second blood inlet conduit and a second blood outlet conduit; and a second pusher plate which makes contact with said second membrane to force blood from said second blood inlet conduit to said second blood outlet conduit.

23. A method of operating an artificial heart assembly having a blood inlet conduit, a blood outlet conduit, and a pumping mechanism for pumping blood from the blood inlet conduit to the blood outlet conduit, said method comprising the steps of:

(a) reversibly driving said pumping mechanism in a first direction and a second direction over a stroke having a length defined by a pair of stroke endpoints, said pumping mechanism being driven at an actual speed which varies over said stroke;

(b) determining said actual speed of said pumping mechanism;

(c) comparing said actual speed of said pumping mechanism with a braking speed; and (d) selectively applying a brake to said pumping mechanism based upon the relative magnitudes of said actual speed and said braking speed.

24. The method as defined in claim 23 additionally comprising the steps of:

(e) detecting a motor stall; and (f) removing said brake upon the detection of a motor stall.

25. The method as defined in claim 23, wherein said step (a) comprises the step of driving said pumping mechanism through a plurality of position bands between said endpoints, wherein said (b) comprises the step of determining said actual speed of said pumping mechanism in one of said position bands of said pumping mechanism, wherein said artificial heart assembly has a plurality of braking speeds stored therein, each of said braking speeds being associated with a different one of said position bands including said one position band, and wherein said step (c) comprises the step of comparing said actual speed of said pumping mechanism in said one position band with said braking speed associated with said one position band.

26. The method as defined in claim 25 additionally comprising the step of modifying one of said braking speeds associated with one of said position bands.

27. The method as defined in claim 25 additionally comprising the steps of:

(e) detecting a motor stall; and (f) increasing one of said braking speeds associated with one of said position bands upon detecting a motor stall.

28. The method as defined in claim 25 additionally comprising the steps of:

(e) detecting when said pumping mechanism moves past one of said endpoints; and (f) decreasing one of said braking speeds associated with one of said position bands upon detecting said pumping mechanism moving past one of said endpoints.

* * * * *

UNITED STATES PATENT AND TRADEMARK OFFICE
CERTIFICATE OF CORRECTION

PATENT NO. : 5,674,281
DATED : October 7, 1997
INVENTOR(S) : ALAN J. SNYDER

It is certified that error appears in the above-indentified patent and that said Letters Patent is hereby corrected as shown below:

On the title page,

Item [57], line 8, "in a opposite" should be --in opposite--.

Column 1, line 54, "in a opposite" should be --in opposite--.

Column 14, line 31, "said (b)" should be --said step (b)--.

Signed and Sealed this

Eighteenth Day of August, 1998

*Attest:*

*Attesting Officer*

BRUCE LEHMAN

*Commissioner of Patents and Trademarks*

UNITED STATES PATENT AND TRADEMARK OFFICE
CERTIFICATE OF CORRECTION

PATENT NO.    : 5,674,281
DATED         : October 7, 1997
INVENTOR(S)   : Alan J. Snyder It is certified that error appears in the above-identified patent and that said Letters Patent is hereby corrected as shown below:

Column 1,
Line 44, please delete "decremented" and insert -- incremented -- therefor.

Column 7,
Line 22, please delete "258" and insert -- 256 -- therefor.

Column 9,
Line 30, please delete "increased" and insert -- decreased -- therefor.

Signed and Sealed this

Sixteenth Day of December, 2003

JAMES E. ROGAN
*Director of the United States Patent and Trademark Office*